(12) United States Patent
Ghouri

(10) Patent No.: US 8,019,619 B2
(45) Date of Patent: Sep. 13, 2011

(54) SYSTEM AND METHOD FOR DYNAMIC ADJUSTMENT OF COPAYMENT FOR MEDICATION THERAPY

(75) Inventor: Ahmed F. Ghouri, San Diego, CA (US)

(73) Assignee: Anvita, Inc., San Diego, CA (US)

( * ) Notice: Subject to any disclaimer, the term of this patent is extended or adjusted under 35 U.S.C. 154(b) by 1874 days.

(21) Appl. No.: 10/680,523

(22) Filed: Oct. 7, 2003

(65) Prior Publication Data

US 2005/0015278 A1    Jan. 20, 2005

Related U.S. Application Data

(60) Provisional application No. 60/488,360, filed on Jul. 17, 2003.

(51) Int. Cl.
*G06Q 10/00* (2006.01)
*G06Q 50/00* (2006.01)

(52) U.S. Cl. ............... 705/2; 705/3; 705/4; 600/300

(58) Field of Classification Search .............. 600/300
See application file for complete search history.

(56) References Cited

U.S. PATENT DOCUMENTS

| | | | |
|---|---|---|---|
| 6,980,958 B1 * | 12/2005 | Surwit et al. ............... | 705/2 |
| 2001/0037216 A1 * | 11/2001 | Oscar et al. ............... | 705/2 |
| 2002/0095314 A1 * | 7/2002 | Bodsworth et al. ........... | 705/2 |
| 2004/0039602 A1 * | 2/2004 | Greenberg et al. ........... | 705/2 |

* cited by examiner

*Primary Examiner* — Gerald J. O'Connor
*Assistant Examiner* — Linh Michelle Le
(74) *Attorney, Agent, or Firm* — Knobbe, Martens, Olson & Bear LLP

(57) ABSTRACT

System and method for the cost-effective use of medications, comprising dynamically adjusting the patient cost for a plurality of possible medication treatment therapies according to the cost-effectiveness of each possible medication therapy based on known patient attributes, and providing a physician with the dynamically determined patient cost of at least one of the possible medication treatment therapies.

19 Claims, 2 Drawing Sheets

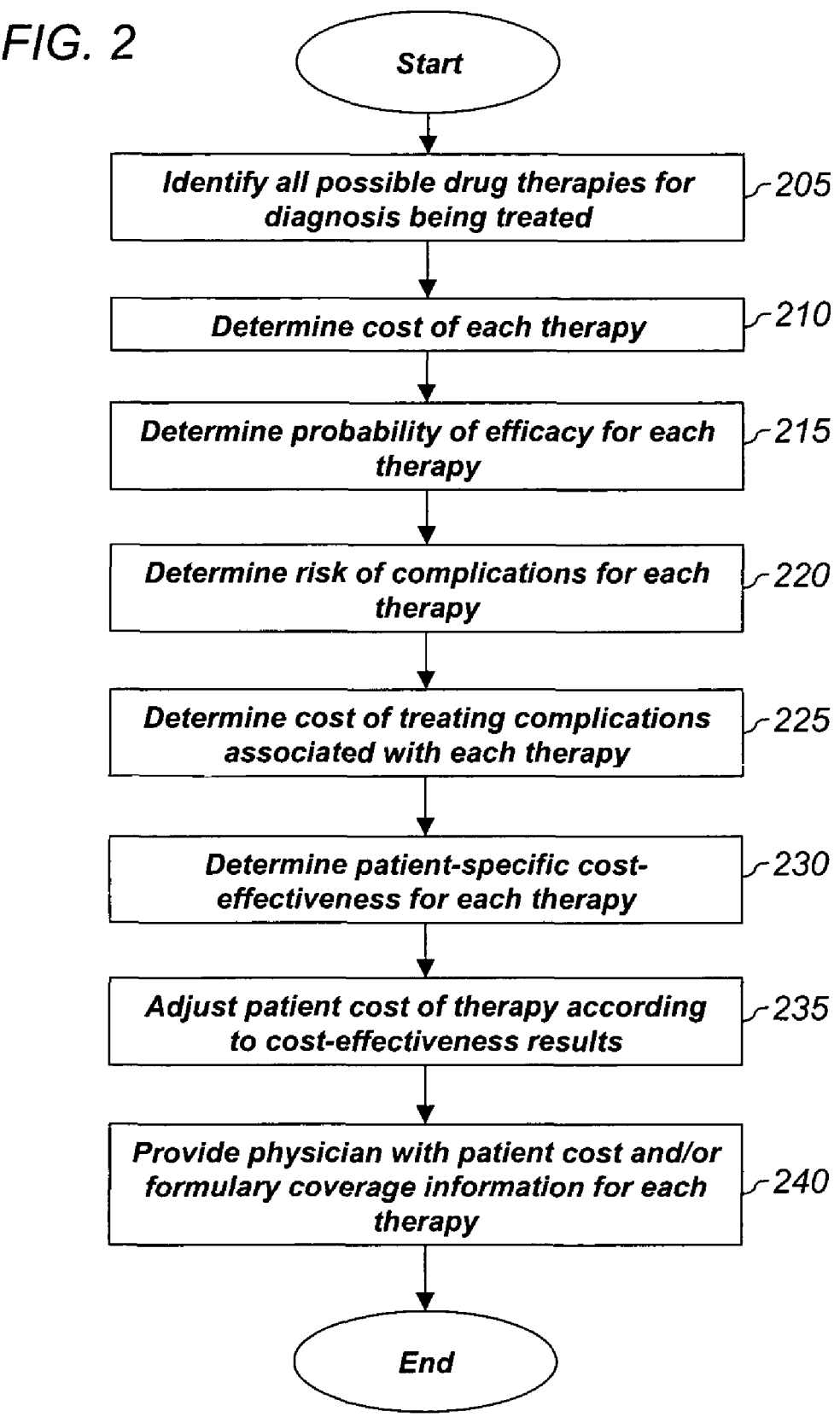

SYSTEM AND METHOD FOR DYNAMIC ADJUSTMENT OF COPAYMENT FOR MEDICATION THERAPY

CROSS REFERENCE TO RELATED APPLICATION

This application claims priority to U.S. Provisional Patent Application 60/488,360 entitled "SYSTEM AND METHOD FOR DYNAMIC ADJUSTMENT OF COPAYMENT FOR MEDICAL TREATMENT" and filed on Jul. 17, 2003. The disclosure of the above-described filed application is hereby incorporated by reference in its entirety.

BACKGROUND OF THE INVENTION

1. Field of the Invention

The present invention relates to the cost effective use of prescription medications, and more particularly to a computerized system and method for dynamically adjusting patient copayments for medications based upon clinical circumstances and patient attributes.

2. Description of the Related Art

Physicians are currently inundated and overwhelmed with guidelines for the most appropriate or cost-effective use of medication therapy based upon a patient's medical history. In one example, for the treatment of an uncomplicated middle ear infection in a young child who is otherwise healthy, there is strong evidence that certain inexpensive generic antibiotics are just as effective yet far cheaper than expensive brand-name medications, and equally safe. Unfortunately, there are currently about 7,500 medical journal articles published per week, and it has become humanly impossible for medical doctors to keep abreast of the latest developments to ensure optimal and/or the most cost-effective care for their patients. However, cost-effective use of medications will be imperative in the future, as drug-related expenditures are increasing at an unsustainable rate, and constitute the largest component of increasing healthcare costs overall.

The problem in adhering to guidelines for the cost-effective use of medications is not one of negligence or disregard by the physician, but sheer information overload. Many studies by sources such as the American Medical Association have demonstrated that letters to doctors, faxes, and articles in journals are largely ineffective at reducing inappropriate use of medications because medical doctors generally do not have the time to read or absorb them. Content delivery, whether by paper, Internet, or hand held computers such as Personal Digital Assistants (PDA's), is not likely to solve this problem because there is no time to search for, read, and retain the information provided, regardless of the method of delivery.

Electronic medical records (EMRs) are becoming widely used by hospitals and medical care facilities, where a patient's medical conditions and attributes are stored in an electronic format. In a patient's electronic medical record, patient characteristics such as diseases, medications, age, laboratory results, and sex are stored in a structured data format. The use of standard catalogs for medical terms in patient electronic records makes the implementation of an electronic medical records system possible and efficient. The US Health and Human Services has recently issued a press release that it will adopt one such catalog, the Systematic Nomenclature of Medicine (SnoMed), as a universal standard for this purpose, and provide it free of charge to all electronic medical record vendors. In this system, virtually all medical terms, including diseases, physical findings, lab abnormalities, etc., have a unique numerical ID associated with each of them. Hence, it becomes possible to algorithmically compare a patient's attributes against a set of guidelines for best practices by determining which patient condition ID values match similar ID values found within the guidelines.

Universal methods for real-time data interchange, such as the wireless Internet, can provide physicians with access to the patient electronic record and clinical guidelines at the point of care, in addition to important economic variables such as which medications are covered by a patient's insurance plan (also referred to as a formulary). Furthermore, for each medication covered by a patient's insurance carrier, or listed on the insurer's formulary, a physician can be immediately informed as to the patient cost for that medication, wherein the patient cost is commonly referred to as the copayment, or copay. However, in current medical insurance plans, formularies and copayments are not patient-specific, but more simplistically plan-specific, where copayments are determined based on average patient statistics for a group that may encompass millions of individuals with a high diversity of medical conditions.

SUMMARY OF THE INVENTION

The method and system of the present invention has several aspects, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Invention" one will understand how the features of this invention provide advantages.

One embodiment includes a method for the cost-effective use of medications, comprising dynamically adjusting the patient cost for a plurality of possible medication treatment therapies according to the cost-effectiveness of each possible medication therapy, and providing a physician with the dynamically determined patient cost of at least one of the possible medication treatment therapies.

In another embodiment of the method, dynamically adjusting the patient cost is based on patient medication treatment therapy history. In yet another embodiment of the method, dynamically adjusting the patient cost is based on at least one patient attribute, and the patient attribute may include one of: age, sex, weight, current medications, disease history, current medical condition, and social history.

Yet another embodiment includes a system for the cost-effective use of medications comprises a user interface, configured to receive input from a user and display information, a cost-effectiveness analysis means, configured to determine the cost-effectiveness of a plurality of medication treatment therapies, and a patient cost adjustment means, configured to adjust the patient cost for each of the medication treatment therapies according to cost-effectiveness data from the cost-effectiveness analysis means, wherein the adjusted patient cost for each medication treatment therapy is displayed on the user interface.

In some embodiments of the system, the cost-effectiveness of a medication treatment therapy is based in part on at least one patient attribute. In yet another aspect of the invention, the cost-effectiveness of a medication treatment therapy is based in part on the risk of complications for the medication treatment therapy.

BRIEF DESCRIPTION OF THE DRAWINGS

FIG. 2 is a flow diagram illustrating one embodiment of a method of dynamically adjusting a patient's copayment.

DETAILED DESCRIPTION OF THE PREFERRED EMBODIMENT

Figure 1:
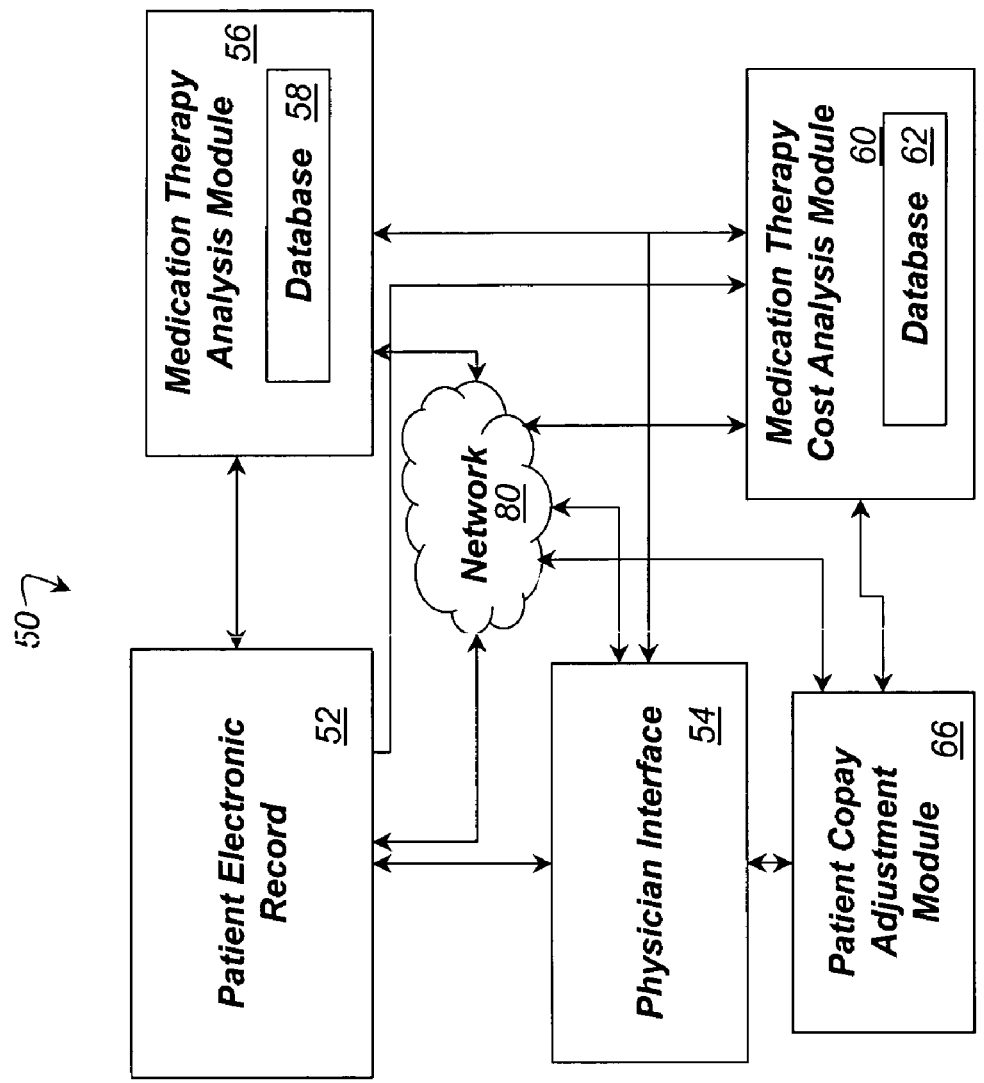
FIG. 1 is a block diagram of one embodiment of a system for patient specific dynamic copayment adjustment.

The following detailed description is directed to certain specific embodiments of the invention. However, the invention can be embodied in a multitude of different ways as defined and covered by the claims. In this description, reference is made to the drawings wherein like parts are designated with like numerals throughout.

In certain embodiments of the copayment adjustment system, three elements are combined to increase the appropriate and cost-effective use of medications in adherence to evidence-based guidelines for optimal clinical practices. The elements include: (1) a structured electronic patient medical history, which may include any subset of age, sex, weight, demographics, coexisting diseases, coexisting medications, allergies, physical findings, and laboratory results, (2) an electronically-maintained list of medications on formulary for that patient, and (3) a collection of guidelines which represent cost-effective therapies, represented in a symbolic machine language (Boolean, for example), which may be applied to a given patient based upon the patient's known attributes. These three elements are used by a dynamic copayment adjustment system to dynamically adjust a patient's copayment for a medication according to the overall cost-effectiveness of the medication as determined using the information in the patient's electronic record.

One embodiment of a system 50 for the dynamic adjustment of a copayment is illustrated in FIG. 1. The system 50 comprises a patient electronic medical record system 52, which maintains a patient electronic record comprising patient attributes relevant to a patient's medical history and clinical guidelines for treatment. As discussed above, the structured patient electronic record can include any subset of patient attributes such as age, sex, weight, demographics, coexisting diseases, coexisting medications, allergies, physical findings, and laboratory results. In one embodiment, each of a patient's medical attributes are defined using standard ID values, such as those used in SnoMed, or similar medical nomenclature standardization.

A physician can view a patient electronic record and enter additional information, including a diagnosis of the patient's current condition and type of medication treatment therapy (such as "antibiotic") at a physician interface 54. As will be appreciated by those skilled in the art, the physician interface 54 can be a desktop, handheld, and/or touchscreen computing device, or any other display and information input device.

A medication therapy analysis module 56 is in data communication with the patient electronic record 52 and the physician interface 54, and is configured to determine possible and appropriate medication treatment therapies and guidelines according to information in the patient electronic record and entered at the physician interface 54. The medication therapy analysis module 56 comprises a database 58, or is in data communication with a database comprising medication treatment therapies, medication effectiveness data, clinical rules, treatment and risk guidelines, etc., examples of which will be discussed in further detail hereinafter.

Substantially all guidelines pertaining to the appropriate use of medications can be rigorously indexed in the database 58 according to medical attributes. In certain embodiments, the database 58 includes medical attributes such as diseases, demographics such as age and sex, use of co-existing medications, laboratory results, physical findings, and social history such as heavy smoking and/or drinking. Systems and software performing the functions of the medication therapy analysis module are known in the art, and will therefore not be discussed in greater detail herein.

The system 50 further comprises a medication therapy cost analysis module 60 in data communication with the medication therapy analysis module 56, patient electronic record 52, and physician interface 54. The medication therapy cost analysis module 60 is configured to analyze the cost of medication therapy treatments determined by the medication therapy analysis module 56 or requested by the physician at the physician interface 54. The medication therapy cost analysis module 60 also comprises a database 62, or is in data communication with a database storing medication therapy cost and cost-effectiveness data. The database 62 can also store medication therapy payment information such as medical insurance information, including formulary coverage and copayment information specific to the patient under treatment. The medication therapy cost analysis module 60 and or database 62 can be provided, for example, by a medical treatment insurer or institution and is not limited as described and illustrated herein.

In one advantageous embodiment, the medication therapy analysis module 56 and/or the medication therapy cost analysis module 60 is implemented according to the system and method for patient-specific optimization of medical therapy by simultaneous symbolic reasoning in all clinical dimensions according to U.S. patent application Ser. No. 10/350,483, filed Jan. 23, 2003, hereby incorporated by reference in its entirety.

A patient copayment adjustment module 66 is coupled to the medication therapy analysis module 60 and the physician interface 54, and is configured to dynamically adjust the patient copayment for medication therapy treatments determined by the medication therapy analysis module 56 or provided by the physician at the physician interface 54. The patient copayment adjustment module 66 adjusts the copayment for each medication treatment therapy according to the cost-effectiveness of each treatment as determined by the medication therapy cost analysis module 60. The patient copayment adjustment module 66 provides a treating physician with adjusted copayment amounts along with medication treatment therapy options such that the physician can make an informed decision in prescribing a medication treatment therapy for a patient under treatment.

It will be appreciated by those skilled in the art that the elements of the system 50 can be coupled to a network 80 such as a local area network (LAN) or wide area network (WAN), and may include wireless communication means such as radiofrequency (RF), 802.11 (WiFi), or Bluetooth, and are not limited to hard-wired connections, but may include any combination of data communication means known in the technology. Furthermore, as can be appreciated by one of ordinary skill in the art, each of the modules described herein comprise various sub-routines, procedures, definitional statements, and macros. The description of each of the modules is used for convenience to describe the functionality of the system 50. Thus, the processes that are undergone by each of the modules may be arbitrarily redistributed to one of the other modules, combined together in a single module, or made available in a shareable dynamic link library. For example, the system 50 may be implemented as or incorporated into a single device such as a PDA.

FIG. 2 is a flow diagram illustrating one method of dynamically adjusting the copayment for a medication treatment therapy. Depending on the embodiment, additional steps may be added, others removed, and the order of the steps rearranged. In a step 205, all possible medication therapies are determined for the diagnosis being treated, or the medication therapies can be determined according to a type of therapy input by a treating physician at the physician interface 54. For example, the physician may input a diagnosis of "pneumonia" or may enter a type of medication therapy such as "antibiotic".

In determining possible medical treatment therapies, the pertinent treatment guidelines can be determined by matching guideline ID values with the ID values stored in the patient electronic record. Multiple guidelines may apply, but they will generally not conflict because a physician will only be evaluating a single dimension (diagnosis) at a time when choosing a medication treatment therapy. For example, a physician will typically not be selecting a high blood pressure medication and an allergy medicine at the same time.

In the rare instances in which there are conflicting results in the application of two or more guidelines, the most important guideline is determined from a clinical perspective using a predefined numerical scoring system. That is, each guideline will have previously been assigned a severity score indicating the importance of adherence to the guideline. For example, a guideline for prevention of a heart attack will have a higher severity score than a guideline to minimize the side effect of a skin rash. The government agency known as the U.S. Preventative Task Force Services currently provides this type of scoring system to some extent for guidelines, although any scoring system may be used.

After possible medication therapies have been determined in step 205, the cost of each of the possible therapies is determined in a step 210, where the cost is based on the data provided, for example, by a patient's medical insurance agency. In a step 215, the probability of efficacy is determined for each possible therapy. Selectively, medication treatment therapies which are dangerous, such as those potentially causing a life-threatening medication interaction, may be filtered out entirely from the available treatment choices to prevent injury. In a step 220, the risk of complications and possible further treatment is determined for each therapy, and the cost of further treatment in the event of complications is determined in a step 225, similar to the determination in step 210.

Following step 225, the overall patient-specific cost-effectiveness of each medication treatment therapy is determined in a step 230, wherein, for example, the cost of the initial medication, along with the likelihood or probability of complications specific to the patient multiplied by the cost of such treatment, provides the patient-specific total cost for that particular medication treatment therapy. The basis for dynamic copayment adjustment is not limited to the risk of additional and/or more severe medical conditions due to the use of the medication in question. For example, for a patient (Patient W) with a history of gastric acid reflux and known failure to respond to antacids known as $H_2$ blockers, the more appropriate treatment may be a medication known as a proton pump inhibitor (PPI), even though it is more expensive than $H_2$ blockers. The more expensive PPI medication is more likely to be the most cost-effective medication for Patient W because the $H_2$ blockers previously used were unsuccessful in treating the patient's medical condition. Prescribing a $2^{nd}$ $H_2$ blocker would likely therefore be a waste of time and money, even if it is not dangerous in the patient.

In a step 235, the patient copayment is adjusted according to the cost-effectiveness of each medication treatment therapy determined in step 230, wherein the most cost-effective treatment is assigned a lower copayment than a less cost-effective treatment. For example, the most cost-effective medication may be assigned a copay of $5 and the least cost-effective would be assigned a copay of $10. Thus, Patient W's copayment for the more expensive medication (the PPI) would be adjusted to be the same as or lower than the copayment for an $H_2$ blocker. Such an adjustment is based on the determination that the use of the PPI medication would be more cost-effective long term because it would be effective in the treatment of the patient's condition, whereas the $H_2$ blocker would not be effective. As will be appreciated by those skilled in the art, the copayment adjustment can be performed according to a predefined algorithm or using tables, for example.

Finally, the possible medication treatment therapies and adjusted copayments or formulary coverage information are presented to the treating physician in a step 240. The treatment therapies are preferably presented in order of lowest to highest copayment, however, they can be listed in any order to encourage selection of a favored medication based on factors other than or in addition to copayment amount.

In certain embodiments, the copayment is adjusted according to the best possible treatment for the patient, wherein the determining whether a treatment is best for a given patient is dependent upon, for example, number and severity of side effects, and length of time for effectively treating the patient. The reduced or adjusted copayment for the best treatment therapy can be applied regardless of whether the treatment is the most cost-effective. In additional embodiments the method further comprises communicating the adjusted copayment information to a pharmacy.

It should be noted that the invention is independent of the specific scoring system used to determine cost-effectiveness, the catalog used for documenting the patient's attributes in the electronic medical record, or the subset of guidelines employed. For instance, an endpoint in cost-effectiveness for anti-hypertensive medications might be dollars per reduction in blood pressure of 10 mm Hg. In general, guidelines are established firstly by reputable bodies, including the U.S. government, based on strong evidence in the literature on their effectiveness when applied. However, embodiments of the invention can also be implemented using proprietary, internally developed guidelines which may be exclusively owned by an insurance company or prescription benefits manager.

It should be noted that guidelines may represent composite hybrids of multiple patient attributes such as demographics, disease, conditions, use of other medications, or laboratory findings. For example, there might be a guideline indicating a therapy which pertains to elderly patients who have recently had a stroke, or pregnant patients with sickle cell anemia. The composition of these guidelines is not controlling, but more importantly the methodology used to determine if they apply, given known information about the patient in an electronically stored format.

It should be noted that the index to each guideline is advantageously a patient attribute, whether disease, medication, age, allergy, or otherwise. As discussed above with respect to certain embodiments of the system, with modern electronic medical records, each of these terms exists as a data object, with unique ID to represent each concept.

Dynamic copayment adjustment in a patient-specific fashion uses a safety score and/or a cost-efficacy score associated with each therapeutic medication choice. It will be appreciated that the type of scoring mechanism is not limited in the present invention and that those described herein are exemplary nature.

In safety scoring, there is generally a multilevel score (as used today by drug interaction checking software programs) in which the severity of an interaction is scored from a range of one to five, with a score of one corresponding to a severe risk of injury, and a score of five corresponding to a rating of harm unlikely. Similarly, for cost-effectiveness, there are a plurality of scoring level and scheme possibilities, each of which are specific to a disease condition.

In one example, there are three cholesterol-lowering medications, Drugs A, B, and C, for comparison in terms of cost-efficiency. One method of measuring this efficiency is the price of each medication for a year's worth of therapy divided by a mean reduction in serum cholesterol, typically measured in units of mg/dL. As it is well established that the risk of a heart attack is directly proportional to the level of serum cholesterol, this measure is clinically appropriate for this class of medications.

In the present example, it has been determined by prior medical research that the cost-effectiveness parameters are already known for cholesterol Drugs A, B, and C, as illustrated in Table 1. Furthermore, there is a known Drug X which can chemically inactivate, to a known but varying degree, each of Drugs A, B, and C. It should be noted that Drug X may be a medication wholly unrelated to the treatment of high cholesterol, for example, Drug X could be an anti-depressant.

TABLE 1

Cost-effectiveness (dollars/mg/dL) for Cholesterol Lowering Medications

|  | Patient Not Taking Drug X | | | Patient Also Taking Drug X | | |
| --- | --- | --- | --- | --- | --- | --- |
|  | Drug A | Drug B | Drug C | Drug A | Drug B | Drug C |
| Cholesterol medication Cost per mg/dL cholesterol reduction | $25 | $50 | $15 | $135 | $60 | $175 |
| Copay | Medium Copay | High Copay | Low Copay | Medium Copay | Low Copay | High Copay |

As shown in Table 1, for a patient not taking Drug X, Drug C is the most cost-effective in reducing cholesterol ($15 per mg/dL reduction vs. $25 and $50 for Drug A and Drug B, respectively). However, in a patient also taking Drug X, the most cost-effective medication is no longer Drug C. In a patient taking Drug X, Drug B is the most cost-effective due to the confounding effects of Drug X. Thus, according to one embodiment of the system, Drug C should be assigned the lowest copayment for a patient not taking Drug X, and Drug B should be assigned the lowest copayment for a patient currently taking Drug X. Note in this example that the actual cost of Drugs A, B, and C is immaterial to what is most cost-effective. More advantageously, the measuring point for cost-effectiveness is the most inexpensive way to prevent a heart attack, not the most inexpensive medication.

The following is a more specific example of dynamic copayment adjustment based upon a guideline according to the age of a patient (Patient Q) for which a physician wishes to prescribe a sedative.

Guideline: In elderly patients over 65 years of age, sedatives which may be prescribed should have short elimination half-lives to avoid oversedation due to impaired metabolism associated with old age.

In this example, the cheapest sedative medication (Drug X) may be the most dangerous to use in an elderly patient because it has a long half-life and can cause persistent sedation. However, Drug X may have the lowest assigned copayment because the entity or institution paying for the medication (payer), typically an insurance company, wants to use the least expensive medication. An insurance company's copayment rates are generally based on what is best for an aggregated group of hundreds of thousands to millions of insured patients, not a specific patient.

In the present example, the patient and payer would hope the physician will use sound clinical judgement when exceptions occur, and not administer Drug X to an elderly patient. However, regardless of the good intent and concern of the physician, substantially all clinical rules and guidelines will not be remembered or considered by a physician when prescribing a medication, and errors in medication prescriptions therefore occur on a colossal scale.

Despite the low copayment (in the standard formulary), Drug X is not the most appropriate medication for Patient Q: due to the risk of further health problems in which the payer will have to pay for unnecessary hospitalization and treatment should Patient Q experience complications in response to the use of Drug X. Thus, if it were known by the prescribing physician that the patient were elderly and that sedatives prescribed to geriatric patients should have short half lives (the Guideline), a sedative with a shorter half-life (Drug Y) and higher copayment would be more appropriate due to the reduced risk of complications and corresponding expensive treatment of complications, even if Drug Y has a higher initial cost. It should be noted that the cost-effective use of medications implies their safe use automatically, because inappropriate prescribing (against labeling instructions or in a patient with known allergy, for example) creates a high risk for costly medical complications as a consequence.

In one embodiment, a system for the cost-effective use of medications dynamically adjusts the copayment for Drug X to be more than Drug Y if Patient Q is elderly, whereas the reverse would be the case in a young patient where the cheaper Drug X would be the most cost-effective. Such an adjustment creates an economic incentive (lower cost to the patient or payer) to use Drug Y instead of Drug X, even if the physician were unaware of the problem associated with Drug X for elderly patients. In the present invention, the physician would, on a large statistical basis, adhere to best-practice guidelines without being expected to memorize a universe of millions of changing clinical rules and guidelines.

The following second specific example illustrates the dynamic copayment adjustment using a guideline based on a co-existing disease or condition in Patient V:

Guideline: Patients with G6PD deficiency should avoid use of medications which can lead to oxidative stress and hemolysis.

Patients with congenital deficiency of the enzyme known as G6PD can have severe, life threatening reactions if they are administered certain medications. The spectrum of medicines which are dangerous in such patients can span an entire class of medications including antihistamines, pain medicines, and antibiotics. For any human to reasonably keep track of these medications is unrealistic, especially as new medications are continually introduced into the marketplace.

In the present example, Patient V is diagnosed with a community acquired pneumonia, and the indicated medication for treatment for an otherwise healthy patient is penicillin. Penicillin is produced by a multitude of manufacturers and is therefore inexpensive and desirable by the payer for the Patient V's treatment. Correspondingly, the copayment for penicillin is expected to be low to encourage its use. However, a low copayment for penicillin is not be desirable for a patient with a G6PD deficiency as it may lead to more serious medical problems requiring additional treatment. Thus, penicillin is assigned a high copayment for Patient V, and a very low copayment for an otherwise healthy patient without a G6PD deficiency.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention.

What is claimed is:

1. A method for incentivizing the cost-effective use of medications, the method comprising:
   storing, in a memory of a computer, medical information for a particular patient, the medical information including diagnostic information and patient attribute information, wherein the diagnostic information comprises information indicative of at least one of symptoms of the patient, a diagnosis of a first disease of a patient, and a type of possible medication treatment therapies, and wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient;
   determining, by a processor of the computer, a plurality of possible medication treatment therapies based at least in part on the diagnostic information for the particular patient;
   determining, by the processor of the computer, a patient copayment for each of a plurality of medication treatment therapies based at least in part of the patient attribute information for the particular patient; and
   displaying the determined patient copayments, thereby incentivizing the selection of one of the medication treatment therapies or another of the medication treatment therapies based on the medication information for the particular patient.

2. The method of claim 1, wherein the patient copayment for at least one of the plurality of medication treatment therapies is based on the overall cost of treatment, including treatment of side-effects related to the medication therapy.

3. A system for incentivizing the cost-effective use of medications, the system comprising:
   a user interface configured to receive input from a user and display information;
   storage means configured to store medical information for a particular patient, the medical information including diagnostic information and patient attribute information, wherein the diagnostic information comprises information indicative of at least one of symptoms of the patient, a diagnosis of a first disease of a patient, and a type of possible medication treatment therapies, and wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient;
   medication treatment therapy means configured to determine a plurality of medication treatment therapies based at least in part on the diagnostic information for the particular patient; and
   patient copayment means configured to determine a patient copayment for each of the medication treatment therapies based at least in part of the patient attribute information for the particular patient, wherein the adjusted copayment for each medication treatment therapy is displayed on the user interface, thereby incentivizing the selection of one of the medication treatment therapies or another of the medication treatment therapies based on the medication information for the particular patient.

4. The system of claim 3, wherein the patient copayment of a medication treatment therapy is based at least in part on the risk of complications for the medication treatment therapy.

5. A medication therapy treatment selection system, the system comprising:
   a user interface configured to receive input from a user and display information;
   a storage configured to store medical information for a particular patient, the medical information including diagnostic information and patient attribute information, wherein the diagnostic information comprises information indicative of at least one of symptoms of the patient, a diagnosis of a first disease of a patient, and a type of possible medication treatment therapies, and wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient;
   a processor in data communication with the user interface and the storage, configured to determine a plurality of possible medication treatment therapies based at least in part on the diagnostic information for the particular patient, to determine a patient copayment for each of the medication treatment therapies based at least in part of the patient attribute information for the particular patient, and to
   provide the determined patient copayments to the user interface for display, thereby incentivizing the selection of one of the medication treatment therapies or another of the medication treatment therapies based on the medication information for the particular patient.

6. The system of claim 5, wherein the medical information for the particular patient is accessible by the user interface.

7. The system of claim 5, wherein the user interface is a wireless communication device.

8. The system of claim 5, wherein at least one of the user interface, the storage, and the processor is coupled to a data communication network.

9. A method of incentivizing the cost-effective use of medication treatment therapies, comprising determining, by a processor of a computer, a patient copayment for at least one of a plurality of possible medication treatment therapies based at least in part on part of patient attribute information for the particular patient, wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient, thereby incentivizing the selection of one of the medication treatment therapies or another of the medication treatment therapies based on the medication information for the particular patient.

10. The method of claim 9, further comprising providing a physician with the patient copayment of at least one of the possible medication treatment therapies.

11. A system for incentivizing the of cost-effective use of medication treatment therapies, comprising means for determining a patient copayment for at least one of a plurality of possible medication treatment therapies based at least in part on part of patient attribute information for the particular patient, wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient, thereby incentivizing the selection of one of the medication treatment therapies or another of the medication treatment therapies based on the medication information for the particular patient.

12. The system of claim 11, further comprising means for providing a physician with the patient copayment of at least one of the possible medication treatment therapies.

13. A method of incentivizing the selecting of a cost-effective medication treatment therapy, the method comprising:
   storing, in a memory of a computer, medical information for a particular patient, the medical information including diagnostic information and patient attribute information, wherein the diagnostic information comprises information indicative of at least one of symptoms of the patient, a diagnosis of a first disease of a patient, and a type of possible medication treatment therapies, and wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient;
   determining, by a processor of the computer, a plurality of possible medication treatment therapies based at least in part on the diagnostic information for the particular patient;
   generating cost-effectiveness data for each of the plurality of possible medication treatment therapies based at least in part on the patient attribute information for the particular patient;
   determining, by the processor in the computer, a patient copayment for each of the medication treatment therapies based on the cost-effectiveness data; and
   displaying the determined patient copayments, thereby incentivizing the selection of one of the medication treatment therapies or another of the medication treatment therapies based on the medication information for the particular patient.

14. The method of claim 13, further comprising transmitting the determined patient copayment for at least one of the plurality of medication treatment therapies to a pharmacy or data center communicating with a pharmacy.

15. A method of determining the copayment for a medication, comprising:
   determining, by a processor of a computer, a patient copayment for at least one medication treatment therapy according to patient attribute information for a particular patient, the patient attribute information comprising information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient; and
   providing a physician with the determined patient copayment of the medication treatment therapy, thereby incentivizing the selection of one of the medication treatment therapies or another of the medication treatment therapies based on the patient attribute information for the particular patient.

16. A device for incentivizing selecting a cost-effective medication treatment therapy, comprising:
   a storage module configured to store medical information for a particular patient, the medical information including diagnostic information and patient attribute information, wherein the diagnostic information comprises information indicative of at least one of symptoms of the patient, a diagnosis of a first disease of a patient, and a type of possible medication treatment therapies, and wherein the patient attribute information comprises information indicative of at least one of an age of the patient, a sex of the patient, a weight of the patient, a medication treatment therapy currently prescribed to the patient, a second disease of the patient different than the first disease, a surgery performed on the patient, an allergy of the patient, a laboratory finding related to the patient, and a social history of the patient;
   a medication treatment therapy determination module, configured to determine at least one medication treatment therapy for a patient based at least in part on the diagnostic information for the particular patient;
   a copayment determination module configured to determine a patient copayment of at least one of the medication treatment therapies determined by the medication treatment therapy determination module based at least in part on the patient attribute information of the particular patient; and
   a display configured to display at least one of the determined medication treatment therapies and the determined patient copayment, thereby incentivizing the selection of one of the medication treatment therapies or another of the medication treatment therapies based on the patient attribute information for the particular patient.

17. The device of claim 16, further comprising a cost-effectiveness analysis module configured to determine the cost-effectiveness of the medication treatment therapy determined by the medication treatment therapy module.

18. The device of claim 16, wherein the cost-effectiveness of the medication treatment therapy is based at least in part on the patient attribute information for the particular patient.

19. The device of claim 16, further comprising a communications means module configured to receive patient information from a patient information database.

* * * * *

UNITED STATES PATENT AND TRADEMARK OFFICE
CERTIFICATE OF CORRECTION

| | | |
|---|---|---|
| PATENT NO. | : 8,019,619 B2 | Page 1 of 1 |
| APPLICATION NO. | : 10/680523 | |
| DATED | : September 13, 2011 | |
| INVENTOR(S) | : Ghouri | |

It is certified that error appears in the above-identified patent and that said Letters Patent is hereby corrected as shown below:

At column 11, line 1, in Claim 11, after "the" delete "of".

At column 12, line 58, in Claim 19, before "module" delete "means".

Signed and Sealed this
Sixth Day of March, 2012

David J. Kappos
*Director of the United States Patent and Trademark Office*